(12) United States Patent
Miller

(10) Patent No.: US 7,956,204 B2
(45) Date of Patent: Jun. 7, 2011

(54) PROCESS FOR THE OXIDATION OF HYDROCARBONS UTILIZING SHAPED BINDERLESS TS-1 ZEOLITE CATALYST

(75) Inventor: Stephen J. Miller, San Francisco, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 12/033,695

(22) Filed: Feb. 19, 2008

(65) Prior Publication Data

US 2008/0146827 A1 Jun. 19, 2008

Related U.S. Application Data

(62) Division of application No. 11/226,609, filed on Sep. 13, 2005, now Pat. No. 7,837,977.

(51) Int. Cl.
C01B 39/00 (2006.01)
C01B 37/00 (2006.01)
C01B 39/04 (2006.01)
C07D 301/12 (2006.01)

(52) U.S. Cl. ......... 549/531; 502/60; 502/242; 423/700; 423/702; 423/704; 423/705; 423/706; 423/707; 423/708

(58) Field of Classification Search .................. 549/531; 502/60, 242; 423/700, 702, 704–708
See application file for complete search history.

(56) References Cited

U.S. PATENT DOCUMENTS

| | | | |
|---|---|---|---|
| 3,094,383 A | 6/1963 | Dzierzanowski et al. | |
| 3,119,656 A | 1/1964 | Stambaugh et al. | |
| 4,058,586 A | 11/1977 | Chi et al. | |
| 4,381,255 A | 4/1983 | Nozemack et al. | |
| 4,410,501 A | 10/1983 | Taramasso et al. | |
| 4,822,899 A * | 4/1989 | Groves et al. | 549/533 |
| 5,558,851 A | 9/1996 | Miller | |
| 5,665,325 A | 9/1997 | Verduijn | |
| 6,521,207 B2 | 2/2003 | Oku et al. | |
| 6,603,027 B1 * | 8/2003 | Catinat et al. | 549/533 |
| 6,710,193 B2 * | 3/2004 | Hasenzahl et al. | 549/529 |
| 6,777,364 B2 | 8/2004 | Yoon et al. | |
| 2004/0014591 A1 | 1/2004 | Muller et al. | |
| 2005/0129952 A1 | 6/2005 | Sawada et al. | |
| 2006/0239906 A1 | 10/2006 | Mueller et al. | |

FOREIGN PATENT DOCUMENTS

| | | | |
|---|---|---|---|
| CN | 1050584 C | * | 3/2000 |
| CN | 1401569 A | * | 3/2003 |
| EP | 0 568 566 B1 | | 3/1995 |
| EP | 1 061 046 B1 | | 9/2007 |
| GB | 2 160 517 A | | 12/1985 |
| WO | WO 94/13584 | | 6/1994 |
| WO | WO 2004/026852 A1 | | 4/2004 |

OTHER PUBLICATIONS

Spinace, E. V. et al., Cyclohexane Oxidation Catalyzed by Titanium Silicalite (TS-1): Overoxidation and Comparison with Other Oxidation Systems, 1995, Journal of Catalysis, 157, pp. 631-635.*
Seijger, G.B.F., "In Situ Synthesis of Binderless ZSM-5 Zeolitic Coatings on Ceramic Foam Supports", Microporous and Mesoporous Materials 39 (2000) 195-204.
Yoo et al.,Characterization and catalytic properties of Ti-ZSM-5 prepared by chemical vapor deposition, Catalyst Letters, 2000, p. 169-173, vol. 66, Science Publishers.

* cited by examiner

Primary Examiner — David M. Brunsman
Assistant Examiner — Kevin M Johnson
(74) Attorney, Agent, or Firm — Richard J. Sheridan; E. Joseph Gess; Michael D. Ross

(57) ABSTRACT

A process for oxidation of hydrocarbon, comprising contacting said hydrocarbon with hydrogen peroxide in the presence of a catalytically effective amount of crystalline, titanosilicate zeolite TS-1 catalyst for a time and at a temperature effective to oxidize said hydrocarbon, wherein the catalyst is in the form of binderless, shaped particles comprising titanosilicate, TS-1 and titanosilicate TS-1 precursors and having a defined cross sectional diameter. Also, a process for epoxidation of olefins using crystalline, titanosilicate zeolite TS-1 catalyst. Also a process for oxidation of hydrocarbon using crystalline, titanosilicate TS-1 catalyst, wherein the catalyst is in the form of binderless, shaped particles having a crystallite size of less than 0.2 micron and a defined cross sectional diameter.

23 Claims, No Drawings

PROCESS FOR THE OXIDATION OF HYDROCARBONS UTILIZING SHAPED BINDERLESS TS-1 ZEOLITE CATALYST

This application is a divisional patent application, and it claims the benefit of the prior nonprovisional application Ser. No. 11/226,609 filed Sep. 13, 2005 now U.S. Pat. No. 7,837,977. This divisional application is being filed as the result of a restriction requirement. The USPTO classification of this divisional application is 502, subclass 64. The assigned art unit of the parent application is 4116.

FIELD OF THE INVENTION

The present invention relates to a process for producing crystalline titanosilicate zeolite TS-1 from a reaction mixture which contains only sufficient water to form zeolite TS-1. As used herein, the terms "titanosilicate zeolite TS-1", "zeolite TS-1", or simply TS-1 refers to zeolites having the framework topology of ZSM-5 which contain titanium atoms in their framework structure.

BACKGROUND

Prior art, methods of preparing crystalline zeolite TS-1 typically produce finely divided crystals which must be separated from an excess of liquid in which the zeolite is crystallized. The liquid, in turn, must be treated for reuse or else be discarded with potentially deleterious environmental consequences. Preparing commercially useful catalytic materials which contain the powdered zeolite also normally requires additional binding and forming steps. Typically, the zeolite powder as crystallized must be mixed with a binder material and then formed into shaped particles or agglomerates, using methods such as extruding, agglomeration, and the like. These binding and forming steps greatly increase the complexity of catalyst manufacture involving zeolitic materials. The additional steps may also have an adverse effect on the catalytic performance of the zeolite so bound and formed.

U.S. Pat. No. 3,094,383, issued Jun. 18, 1963 to Dzierzanowski et al., discloses a method for making type A zeolites in the form of coherent polycrystalline aggregates by forming reaction masses consisting of a mixture of sodium aluminate, a siliceous material and water, wherein the $H_2O/Na_2O$ mole ratio is 5 to 25. The mass is aged while maintaining it out of contact with an external aqueous liquid phase while preventing the mass from dehydrating. The aging step can include maintaining the mass at 100° F. (38° C.) for, e.g., 18 hours, followed by heating at 200° F. (93° C.) for, e.g., 24 hours.

U.S. Pat. No. 3,119,659, issued Jan. 28, 1964 to Taggart et al., discloses a method for producing an aluminosilicate zeolite in a preformed body by providing an unreacted preformed body containing a reactive kaodlin-type clay and alkali metal hydroxide, and reacting the preformed body in an aqueous reaction mixture until crystals of the zeolite are formed in the body. The aggregate of the preformed body and the aqueous reactant; mixture has a $H_2O/Na_2O$ mole ratio of at least 20.

U.S. Pat. No. 4,058,586, issued Nov. 15, 1977 to Chi et al., discloses a method for preparing zeolitic aluminosilicates, particularly those that are characterized by pores in the 4 to 10 Angstrom sizes that are designated Zeolites A and X, in which compacts of Zeolites A and X, metakaolin clay mixture undergo crystallization at a temperature of 200° to 700° F. (93° to 371° C.). The crystallization is carried out in a calciner or other drying equipment. Normally, the formed particles furnish all of the liquid needed for crystallization, though steam may be added during the crystallization process.

WO 94/113584, published Jun. 23, 1994, discloses a method for preparing a crystalline aluminosilicate zeolite from a reaction mixture containing only sufficient water so that the reaction mixture may be shaped if desired. In the method, the reaction mixture is heated at crystallization conditions and in the absence of an external liquid phase, so that excess liquid need not be removed from the crystallized material prior to drying the crystals.

GB 2,160,517 A, published Dec. 24, 1985, relates to a preformed synthetic zeolite selected from the group consisting of Y, omega zeolite, offretite, erionite, L zeolite and ferrierite whose Si/Al atomic ratio ranges from 1.5 to 100, the preformed zeolite being obtained from a preformed aluminosilicic material whose Si/Al atomic ratio is lower than that of the product and ranges from 0.5 to 90 by treating the material with a silica-containing product in the presence of at least one organic or inorganic base.

U.S. Pat. No. 5,558,851, issued Sep. 24, 1996 to Miller, discloses a method for preparing a crystalline aluminosilicate zeolite from a reaction mixture containing only sufficient water so that the reaction mixture may be shaped if desired. The reaction mixture is heated under crystallization conditions and in the absence of an external liquid phase, so that excess liquid need not be removed from the crystallized material prior to drying the product. U.S. Pat. No. 5,558,851 is incorporated herein by reference in its entirety.

Titanosilicate zeolite TS-1 is known. See, for example, U.S. Pat. No. 4,410,501, issued Oct. 18, 1983 to Taramasso et al. in which TS-1 and a method for making it are disclosed. U.S. Pat. No. 4,410,501 is incorporated by reference herein in its entirety.

SUMMARY OF THE INVENTION

There is provided a process for oxidation of hydrocarbon, comprising contacting said hydrocarbon with hydrogen peroxide in the presence of a catalytically effective amount of crystalline, titanosilicate zeolite TS-1 catalyst for a time and at a temperature effective of oxidize said hydrocarbon, wherein the catalyst is in the form binderless, shaped particles comprising titanositicate TS-1 and titanosilicate TS-1 precursors, and wherein the particles have a cross sectional diameter between about 1/32 inch and about 1/2 inch.

There is also provided a process for epoxidation of olefins, comprising contacting said olefins with hydrogen peroxide in the presence of a catalytically effective amount of crystalline, titanosilicate zeolite TS-1 catalyst for a time and at a temperature effective to epoxidize said olefins;

a. wherein the catalyst is in the form of a binderless, shaped particle comprising titanosilicate TS-1 and titanosilicate TS-1 precursors;

b. wherein the olefins comprise $C_2$-$C_{30}$ olefins having the general structure:

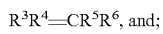

$R^3R^4$=$CR^5R^6$, and;

c. wherein $R^3$, $R^4$, $R^5$ and $R^6$ are the same or different, and are selected from the group consisting of hydrogen and $C_1$-$C_{20}$ alkyl.

There is also provided a process for oxidation of hydrocarbon, comprising contacting said hydrocarbon with hydrogen peroxide in the presence of a catalytically effective amount of crystalline, titanosilicate zeolite TS-1 catalyst for a time and at a temperature effective oxidize said hydrocarbon; wherein the catalyst is in the form of binderless, shaped particles comprising titanosilicate TS-having a crystallite size of less than 0.2 micron; and wherein the particles have a cross sectional diameter between about 1/32 and about 1/2 inch.

DETAILED DESCRIPTION OF THE INVENTION

Description of Zeolite TS-1

Zeolite TS-1 and its X-ray diffraction pattern are disclosed in U.S. Pat. No. 4,410,501 issued Oct. 18, 1983 to Taramasso. It is to be understood that by referencing this patent, it is intended that identification of zeolite TS-1 be is resolved on the basis of its X-ray diffraction pattern. The present invention includes the preparation of zeolite TS-1 regardless of its silica/titanium oxide mole ratio. Thus, reference to this patent is not to be construed as limiting the present invention to the preparation of zeolite TS-1 having the silica/titanium oxide mole ratios disclosed in that patent. It is the framework topology, as identified by the X-ray diffraction pattern, which establishes the identity of the zeolite TS-1.

Preparing the Reaction Mixture

The reaction mixture from which and in which the zeolite TS-1 is crystallized comprises at least one active source of silica, at least one active source of titanium oxide, a nitrogenated organic base capable of forming crystals of TS-1, and sufficient water to form the zeolite TS-1. This amount of water is considerably less than that required in conventional processes for preparing zeolite TS-1.

The amount of water required in the reaction mixture of the present invention is that amount which is needed to adequately blend the mixture. Thus, a reaction mixture is prepared by mixing water with active sources of the zeolite to form a uniform mass having preferably a heavy paste-like consistency. The active sources will be in a form which can be easily-blended into a uniform mass, and may be, for example, powders, hydrated particles, or concentrated solutions. Sufficient water is added to wet all the powders during mixing and kneading of the reaction mixture. Alternatively, sufficient water is added that the powders may be kneaded into a uniform and generally homogeneous mixture which may be shaped. It is not necessary that all of the active sources be readily soluble in water during kneading, since the water added to the active sources will be insufficient to make a fluid-like mixture. The amount of water added depends on the mixing apparatus and on the active sources employed. Those familiar with the art can readily determine without undue experimentation the amount of liquid required to properly mix active sources of the zeolite. For example, hydrated sources of the zeolite may require relatively less water, and dried sources may require relatively more. Though it is preferred that the mixture be blended and kneaded until the mixture has a uniform, homogeneous appearance, the length of time devoted to kneading the mixture is not critical in the present invention.

The water content of the reaction mixture after blending and kneading may be further adjusted, for example, by drying or by the addition of water. When it desired that the reaction mixture be formed into a shape (such as by extrusion), adjusting the amount of water can facilitate shaping the reaction mixture and ensure that it will be self-supporting, i.e., the shape will not collapse or "melt" due to an excess of water in the reaction mixture.

Typical sources of silicon oxide ($SiO_2$) include silicates, silica hydrogel, silicic acid, colloidal silica, fumed silica, tetraalkylotrthosilicates silica hydroxides, precipitated silica and clays. Preferred sources of silicon oxide are solid, essentially aluminum-free, amorphous silicas. Ultrasil® VN3SP silica available from Degussa, having an aluminum content less than about 0.2 wt.% aluminum is a preferred source of silicon oxide.

The titanosilicate zeolites of this invention should be free of aluminum in order to perform optimally as oxidation catalysts. It is, however, possible that traces of aluminum may be introduced into the zeolite from, e.g., a silica source which contains minor amounts of aluminum. If this occurs, the protons associated with the aluminum should be replaced with ammonium, alkali metal or alkaline earth cations. Thus, it is important that the silica source be as free of aluminum as possible.

Typical sources of titanium include hydrolysable titanium compounds, $TiCl_4$, $TiOCl_2$, $Ti(alkoxy)_4$, tetraalkylorthotitanates (such as tetraethylorthotitanate). In addition, coprecipitates comprised of both silicon and titanium (such as W. R. Grace's Si—Ti Type III/2) can be used as a starting reagent. A preferred source of titanium is $Ti(alkoxy)_4$, such as $Ti(butoxide)_4$. The titanium source may be dissolved in a solvent, such as isopropyl alcohol.

Unlike the preparation of aluminosilicate zeolites, the reaction mixture for preparing the titanium-containing zeolites of this invention should not contain alkali metal hydroxide. The presence of alkali metal cations in the reaction mixture can give rise to an undesirable titanium phase in the final product. In addition, all of the hydroxide ions needed in the reaction mixture are supplied by the structure directing agent (SDA), also sometimes called an organic templating agent.

The SDA's useful in the present invention are quaternary ammonium cations capable of forming crystals of TS-1. Examples of quaternary ammonium cations include, but are not limited to tetraalkylammonium cations. Since alkali metals are to be avoided, it is preferred that the counterion for the quaternary ammonium cation be hydroxide to serve as the source of hydroxide for the reaction mixture. The tetraalkylammonium cations include tetrapropylammonium cation (TPA) and tetraethylammyonium cation (TEA). It should be noted that TEA may form crystals with the framework topology of zeolite Beta, so if TEA is used as the SDA it may be necessary to use it in combination with TPA. The SDA should be used in an amount sufficient to form crystals of TS-1. This amount will vary depending upon the relative amounts of the other components of the reaction mixture.

The reaction mixture should contain the following components in the amounts indicated (expressed; as mole ratios of oxides even though the actual starting materials may not be oxides);

|  | General | Preferred |
| --- | --- | --- |
| $SiO_2/TiO_2 =$ | 25-500 | 30-150 |
| $OH^-/SiO_2 =$ | 0.04-0.30 | 0.06-0.15 |
| $H_2O/SiO_2 =$ | 0.5-3 | 0.7-2 |
| $Q/SiO_2 =$ | 0.04-0.30 | 0.06-0.15 | where Q is the SDA.

Forming the Shapes

One advantage of the present invention is that the reaction mixture may be formed into a desired shape before the crystallization step, thereby reducing the number of process steps required to prepare catalytic materials containing the resulting zeolite. Prior to forming the reaction mixture, it may be necessary to change the liquid content of the reaction mixture, either by drying or by adding more liquid, in order to provide a formable mass which retains its shape. In general, for most shaping methods, water will generally comprise from about 20 percent to about 60 percent by weight, and preferably from about 30 percent to about 50 percent by weight of the reaction mixture.

The reaction mixture can be formed into a shape, referred to herein as "particles". Methods for preparing such shapes are well known in the art, and include, for example, extrusion, granulation, agglomerization and the like. When the shape is in the form of particles, they are preferably of a size and shape desired for the ultimate catalyst, and may be in the form of, for example, extrudates, cylinders, spheres, granules, agglomerates and prills. The particles will generally have a cross sectional diameter between about 1/64 inch and about 1/2 inch, and preferably between about 1/32 inch and about 1/4 inch, i.e., the particles will be of a size to be retained on a 1/64 inch and preferably on a 1/32 inch screen and will pass through a 1/2 inch, and preferably through a 1/4 inch screen.

The shape prepared from the reaction mixture will contain sufficient water to retain a desired shape. Additional water is not required in the mixture in order to initiate or maintain crystallization within the shaped reaction mixture. Indeed, it may be preferable to remove some of the excess water from the shaped reaction mixture prior to crystallization. Conventional methods for drying wet solids can be used to dry the reaction mixture, and may include, for example drying in air or an inert gas such as nitrogen or helium at temperatures below about 200° C. and at pressures from subatmospheric to about 5 atmospheres pressure.

It should be noted that, while the reaction mixture of the present invention is capable of being formed into and retaining a shape, it need not be shaped prior to formation of the TS-1 crystals. For instance, the reaction mixture may be in the form of a paste-like mass having no particular shape or profile. Also, the resulting TS-1 product need not have any particular shape and may, in fact, simply be in the form of a powder.

Zeolite Crystallization

According to the present process, the zeolite is crystallized either within the reaction mixture or within the shape made from the reaction mixtures. In either case, the composition of the mixture from which the zeolite is crystallized has the molar composition ranges stated above.

It is preferred that the total volatiles content of the reaction mixture during crystallization be in the range of between about 20 wt. % and about 60 wt. % and preferably between about 30 wt. % and about 60 wt. %, based on the weight of the reaction mixture, where the total volatiles content is the measure of total volatile liquid, including water, in the reaction mixture. It is a feature of the present process that no additional liquid beyond that required to produce the zeolite TS-1 is required for zeolite crystallization.

Crystallization of the zeolite takes place in the absence of an added external liquid phase, i.e., in the absence of a liquid phase separate from the reaction mixture. In general, it is not detrimental to the present process if some liquid water is present in contact with the reaction mixture during crystallization, and it can be expected that some water may be on the surface of the reaction mixture during crystallization, or that some water may be expelled from the reaction mixture and may collect on or near the reaction mixture as the reaction progresses. However, it is an objective of the present invention to provide a method of crystallizing the zeolite in such a way as to minimize the amount of water which must be treated and/or discarded following crystallization. To that end, the present method provides a zeolite synthesis method which requires no additional water for crystallization beyond a sufficient amount of liquid required to form the zeolite TS-1.

Crystallization is conducted at an elevated temperature and usually in an autoclave so that the reaction mixture is subject to autogenous pressure until the crystals of zeolite are formed. The temperatures during the hydrothermal crystallization step are typically maintained from about 90° C. to about 200° C., preferably from about 100° C. to about 170° C.

The crystallization is conducted under conditions which will prevent dehydration of the reaction mixture. This may be accomplished by exposing the reaction mixture to a small amount of water vapor or steam during crystallization.

The crystallization time required to form crystals will typically range from about 1 hour to about 10 days, and more frequently from about 3 hours to about 4 days. Under certain circumstances, crystallization times of less than 24 hours are required to prepare crystallized material of high crystallinity. In the present method, the crystallized material collected following the crystallization step will typically comprise at least about 50 weight percent crystals. Crystallized material containing at least about 80 weight percent crystals, and even at least about 90 weight percent crystals, may also be prepared using the present method.

Once the zeolite crystals have formed, the crystals may be water-washed and then dried, e.g., at 90° C. to 150° C. for from 8 to 24 hours. The drying step can be performed at atmospheric or subatmospheric pressures.

Due to the unpredictability of the factors which control nucleation and crystallization in the art of crystalline oxide synthesis, not every combination of reagents, reactant ratios, and reaction conditions will result in crystalline products. Selecting crystallization conditions which are effective for producing crystals may require routine modifications to the reaction mixture or to the reaction conditions, such as temperature, and/or crystallizaton time. Making these modifications are well within the capabilities of one skilled in the art.

Seed Crystals

The zeolite made by the present process is crystallized within the reaction mixture, which comprises amorphous reagents. Crystalline material (i.e., "seed" crystals of zeolite TS-1) may be added to the mixture prior to the crystallization step, and methods for enhancing the crystallization of zeolites by adding "seed" crystals are well known. However, the addition of seed crystals is not a requirement of the present process. Indeed, it is an important feature of the present process that the zeolite can be crystallized within the reaction mixture in the absence of crystals added prior to the crystallization step. When seed crystals are used, typically about 0.1% to about 10% of the weight of the silica used in the reaction mixture is added.

Zeolite Crystallite Size

Typically, the crystallite size of the TS-1 made in accordance with this invention is less than about 0.2 micron as determined by Scanning Electron Microscopy. As used herein, the term "crystallite size" refers to the longest dimension of the crystal.

The crystallite size of the zeolite may be determined by, for example, grinding the shaped particles to separate the individual crystals. High resolution electron micrographs of the separated crystals can then be prepared after which the average size of individual zeolite crystals can be determined by reference to calibrated length standards. An average crystallite size may then be computed in various well-known ways including:

$$\text{Number Average} = \frac{\sum_{i=1}^{n}(n_i \times L_i)}{\sum_{i=1}^{n} n_i}$$

where $n_i$ is the number of zeolite crystals where minimum length falls within an interval $L_i$. For purposes of this invention, average crystal size will be defined as a number average.

It is important to note that for purposes of this invention, zeolite crystallite size is distinguished from what some manufacturers term "zeolite particle size," the latter being the average size of all particles, including both individual crystals and polycrystalline agglomerates, in the as-produced zeolite powder.

Binderless Catalyst

One advantage of the present invention is that the TS-1 catalyst may be prepared in a form that can be used without the necessity of adding a binder to the catalyst. Thus, a shaped TS-1 catalyst can be made without the additional step of adding a binding to the TS-1 and then shaping (e.g., extruding) the bound TS-1. This can be important if the binders that would ordinarily be used can be a source of undesirable aluminum.

Thus, the catalysts of the present invention can be in the form of a shaped, binderless catalyst comprising essentially all TS-1 and TS-1 precursors. As used herein, the term "TS-1 precursors" refers to components of the reaction mixture, primarily the sources of silica and titanium oxide and the quaternary ammonium cation, which may remain unreacted in the final product. "Essentially all" refers to the fact that the catalyst is at least 90 weight percent, preferably at least 95 weight percent, TS-1 and TS-1 precursors. It should be noted that if the reaction to form the TS-1 crystals is complete and the quaternary ammonium cation is completely removed, the catalyst will comprise essentially all TS-1 with no TS-1 precursors present.

The TS-1 of the present invention is useful in catalysts for oxidation reactions, such as the following;

Oxidation Reactions

The TS-1 prepared by the process of this invention is useful as a catalyst in the oxidation of hydrocarbons Examples of such reactions include, but are not limited to, the epoxidation of olefins, oxidation of alkanes and the oxidation of cyclohexane.

The amount of TS-1 catalyst employed is not critical, but should be sufficient so as to substantially accomplish the desired oxidation reaction in a practicably short period of time. The optimum quantity of catalyst will depend upon a number of factors including reaction temperature, the reactivity and concentration of the hydrocarbon substrate, hydrogen peroxide concentration, type and concentration of organic solvent, as well as the activity of the catalyst. Typically, however, the amount of catalyst will be from about 0.001 to 10 grams per mole of hydrocarbon.

Typically, the titanium-containing crystalline zeolites of this invention are thermally treated (calcined) prior to use as a catalyst.

The oxidizing agent employed in the oxidation processes of this invention is a hydrogen peroxide source such as hydrogen peroxide ($H_2O_2$) or a hydrogen peroxide precursor (i.e., a compound which under the oxidation reaction conditions is capable of generating or liberating hydrogen peroxide).

The amount of hydrogen peroxide relative to the amount of hydrocarbon substrate is not critical, but must be sufficient to cause oxidation of at least some of the hydrocarbon. Typically, the molar ratio of hydrogen peroxide to hydrocarbon is from about 100:1 to about 1:100 preferably 10:1 to about 1:10. When the hydrocarbon is an olefin containing more than one carbon-carbon double bond, additional hydrogen peroxide may be required. Theoretically, one equivalent of hydrogen peroxide is required to oxidize one equivalent of a mono-unsaturated substrate, but it may be desirable to employ an excess of one reactant to optimize selectivity to the epoxide. In particular, the use of a small to moderate excess (e.g., 5 to 50%) of olefin relative to hydrogen peroxide may be advantageous for certain substrates. If desired, a solvent may additionally be present during the oxidation reaction in order to dissolve the reactants other than the TS-1 to provide better temperature control, or to favorably influence the oxidation rates and selectivities. The solvent, if present, may comprise from 1 to 99 weight percent of the total oxidation reaction mixture and is preferably selected such that it is a liquid at the oxidation reaction temperature. Organic compounds having boiling points at atmospheric pressure of from about 25° C. to about 300° C. are generally preferred for use. Excess hydrocarbon may serve as a solvent or diluent. Illustrative examples of other suitable solvents include, but are not limited to, ketones (e.g., acetone, methyl ethyl ketone, so acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl alcohol, alpha-methyl benzyl alcohol, cyclohexanol). More than one type of solvent may be utilized. Water may also be employed as a solvent or diluent.

The reaction temperature is not critical, but should be sufficient to accomplish substantial conversion of the substrate hydrocarbon within a reasonably short period of time. It is generally advantageous to carry out the reaction to achieve as high a hydrogen peroxide conversion as possible, preferably at least about 50%, more preferably at least about 90%°, most preferably at least about 95%, consistent with reasonable selectivities. The optimum reaction temperature will be influenced by catalyst activity, to hydrocarbon reactivity, reactant concentrations, and type of solvent employed, among other factors, but typically will be in a range of from about 0° C. to about 150° C. (more preferably from about 25° C. to about 120° C.).

Reaction or residence times from about one minute to about 48 hours (more desirably from about ten minutes to about eight hours) will typically be appropriate, depending upon the above-identified variables. Although subatmospheric pressures can be employed, the reaction is preferably performed at atmospheric or at elevated pressure (typically, between one and 100 atmospheres), especially when the boiling point of the hydrocarbon substrate is below the oxidation reaction temperature. Generally, it is desirable to pressurize the reaction vessel sufficiently to maintain the reaction components as a liquid phase mixture. Most (over 50%) of the hydrocarbon substrate should preferably be present in the liquid phase.

The oxidation process of this invention may be carried out in a batch, continuous, or semi-continuous manner using any appropriate type of reaction vessel or apparatus such as a fixed bed, transport bed, fluidized bed, stirred slurry, or CSTR reactor. The reactants may be combined all at once or sequentially. For example, the hydrogen peroxide or hydrogen peroxide precursor may be added incrementally to the reaction zone. The hydrogen peroxide could also be generated in situ within the same reactor zone where oxidation is taking place.

Once the oxidation has been carried out to the desired degree of conversion, the oxidized product may be separated and recovered from the reaction mixture using any appropriate technique such as fractional distillation extractive distillation) liquid-liquid extraction) crystallization, or the like.

Olefin Epoxidation

One of the oxidation reactions for which TS-1 is useful as a catalyst is the epoxidation of olefins. The olefin substrate epoxidized in the process of this invention may be any organic compound having at least one ethylenically unsaturated functional group (i.e., a carbon-carbon double bond) and may be a cyclic, branched or straight-chain olefin. The olefin may contain aryl groups (e.g., phenyl, naphthyl). Preferably, the olefin is aliphatic in character and contains from 2 to about 30 carbon atoms. The use of light (low-boiling) $C_2$ to $C_{10}$ mono-olefins is especially advantageous.

More than one carbon-carbon double bond may be present in the olefin, i.e., dienes, trienes and other polyunsaturated substrates may be used. The double bond may be in a terminal or internal position in the olefin or may alternatively form part of a cyclic structure (as in cyclohexene, for example).

Other examples of suitable substrates include unsaturated fatty acids or fatty acid derivatives such as esters or glycerides, and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy) thiol) nitro, cyano, ketone) acyl, ester, anhydride, amino, and the like.

Exemplary olefins suitable for use in the process of this invention include ethylene, propylene, the butenes (i.e., 1,2-butene, 2)-3-butene) isobutylene), butadiene, the pentenes, isoprene) 1-hexene, 3-hexene, 1-heptene, 1-octene, diisobutylene, 1-nonene 1-tetradecene, pentamyrcene, camphene, 1-undecene, 1-dodecene 1-tridecene) 1-tetradecene, 1-pentadecene, 1-hexadecene, 1-heptadecene, 1-octadecene, 1-nonadecene, 1-eicosene, the trimers and tetramers of propylene, styrene (and other vinyl aromatic substrates), polybutadienes, polyisoprene cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane vinyl cyclohexane, vinyl cyclohexene, methallyl ketone, allyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters) and the like.

Olefins which are especially useful for epoxidation are the $C_2$-$C_{30}$ olefins having the general structure

wherein $R^3$, $R^4$, $R^5$ and $R^6$ are the same or different and are selected from the group consisting of hydrogen and $C_1$-$C_{20}$ alkyl.

Mixtures of olefins may be epoxidized and the resulting mixtures of epoxides either employed in the mixed form or separated into the different component epoxides.

EXAMPLES

There are numerous variations on the embodiments of the present invention illustrated in the Examples which are possible in light of the teachings supporting the present invention. It is therefore understood that within the scope of the following claims, the invention may be practiced otherwise than as specifically described or exemplified.

Example 1

Preparation of Titanosilicate Zeolite TS-1 Using Ti(butoxide)$_4$

A reaction mixture was prepared by placing 100 grams of Ultrasil®VN3SP silica in a Baker-Perkins mixer. Sixty-five grams of 40 wt. % tetrapropylammonium hydroxide (TPAOH) was added to the mixer and mixed with the silica for 30 minutes. Eight grams of Ti(butoxide)$_4$ was dissolved in 20 grams of isopropyl alcohol and added to the mixer, followed by 35 grams of water. The mixture was then mixed until a uniform paste was obtained. It is important that the Ti(butoxide)$_4$ be thoroughly dispersed throughout the paste. No binder is added to the paste.

The paste was dried to an extrudable consistency and extruded with a Carver press using a 1/12 inch die. Half of the extrudate was dried to 47% volatiles, and the other half was dried to 43% volatiles.

Both batches were crystallized in an autoclave at autogenous pressure at 150° C. for 24 hours. The resulting products were binderless extrudates containing essentially 100% titanosilicate zeolite TS-1 as determined by X-ray diffraction analysis and infra-red spectroscopy (as described in aforementioned U.S. Pat. No. 4,410,501). The extrudates contained crystals of TS-1 having a crystallite is size of less than about 0.2 micron, as determined by Scanning Electron Microscopy.

Example 2

Preparation of Titanosilicate Zeolite TS-1 Using Ti(butoxide)$_4$

Titanosilicate zeolite TS-1 was prepared by the procedure of Example 1, except that the Ti(butoxide)$_4$ was mixed with the TPAOH (without isopropyl alcohol) prior to addition to the mixer. The resulting product was binderless extrudates containing essentially 100% titanosilicate zeolite TS-1 as determined by X-ray diffraction analysis and infra-red spectroscopy (as described in aforementioned U.S. Pat. No. 4,410,501). The extrudates contain crystals of TS-1 having a crystallite size of less than about 0.4 micron, as determined by Scanning Electron Microscopy ("SEM").

What is claimed is:

1. A process for oxidation of hydrocarbons, comprising preparing a shaped and binderless catalyst by:
   (A) preparing a reaction mixture comprising at least one active source of silica and at least one hydrolysable titanium compound in amounts sufficient to produce zeolite TS-1, at least one quaternary ammonium cation capable of forming crystals of TS-1, and an amount of water sufficient to produce TS-1;
   (B) forming the reaction mixture into a shape without a binder; and
   (C) heating the reaction mixture under crystallization conditions and in the absence of an added external liquid phase for a time sufficient to form crystals of TS-1, and then
   (D) contacting the hydrocarbons with a catalytically effective amount of the titanosilicate zeolite TS-1 catalyst in the presence of an oxidizing agent for a time and at a temperature effective to oxidize the hydrocarbons.

2. The process of claim 1, wherein the process for oxidation of hydrocarbons is selected from the group consisting of a process for epoxidation of olefins, a process for oxidation of alkanes, and a process for oxidation of cyclohexane.

3. The process of claim 1, wherein the oxidizing agent is selected from the group consisting of hydrogen peroxide and hydrogen peroxide precursors.

4. The process of claim 1, wherein the oxidizing agent is hydrogen peroxide, and wherein the contacting is performed in a reaction mixture having a ratio of the hydrogen peroxide to hydrocarbon from about 100:1 to about 1:100.

5. The process of claim 1, wherein the oxidizing agent is hydrogen peroxide, and wherein the contacting is performed in a reaction mixture having a ratio of the hydrogen peroxide to hydrocarbon from about 10:1 to about 1:10.

6. The process of claim 1, wherein the process for oxidation of hydrocarbons is a process for epoxidation of olefins.

7. The process of claim 6, wherein the olefin is a C2-C30 olefin having the general structure $R^3R^4C\!\!=\!\!CR^5R^6$, wherein $R^3$, $R^4$, $R^5$ and $R^6$ are the same or different, and are selected from the group consisting of hydrogen and $C_1$-$C_{20}$ alkyls.

8. The process of claim 6, wherein the olefins are a mixture of olefins.

9. The process of claim 1, wherein the catalyst is a particle having a cross sectional diameter between about 1/64 inch and about 1/2 inch.

10. The process of claim 1, wherein the catalyst is a particle having a cross sectional diameter between about 1/32 inch and about 1/4 inch.

11. The process of claim 1, wherein the catalyst is a particle having a cross sectional diameter between about 1/32 inch and about 1/2 inch.

12. The process of claim 1, wherein the catalyst is a particle having a cross sectional diameter between about 1/64 inch and about 1/4 inch.

13. The process of claim 1, wherein the catalyst is a particle in a form selected from the group consisting of extrudates, cylinders, spheres, granules, agglomerates, and prills.

14. The process of claim 1, wherein the catalyst comprises at least 95 weight percent combined titanosilicate TS-1 and titanosilicate TS-1 precursors.

15. The process of claim 1, wherein the catalyst comprises essentially all titanosilicate TS-1 and no titanosilicate TS-1 precursors.

16. The process of claim 1, wherein the titanosilicate TS-1 has a crystallite size of less than 0.2 micron.

17. The process of claim 1, wherein the titanosilicate TS-1 is free of aluminum.

18. The process of claim 1, wherein the reaction mixture has a water/silica molar ratio during crystallization of no greater than about 3.

19. The process of claim 18, wherein the reaction mixture during crystallization has a water/silica molar ratio between about 0.7 and about 2.

20. The process of claim 1, wherein the reaction mixture has the following molar composition ranges:

| | |
|---|---|
| $SiO_2/TiO_2 =$ | 25-500 |
| $OH^-/SiO_2 =$ | 0.04-0.30 |
| $H_2O//SiO_2 =$ | 0.5-3 |
| $Q/SiO_2 =$ | 0.04-0.30 | where Q is the quaternary ammonium cation.

21. The process of claim 1, wherein said reaction mixture has the following molar com position ranges:

| | |
|---|---|
| $SiO_2/TiO_2 =$ | 30-150 |
| $OH^-/SiO_2 =$ | 0.06-0.15 |
| $H_2O//SiO_2 =$ | 0.7-2 |
| $Q/SiO_2 =$ | 0.06-0.15. |

22. The process of claim 1, wherein the quaternary ammonium compound is a tetraalkylammonium cation.

23. The process of claim 22, wherein the tetraalkylammonium compound is a tetrapropylammonium cation.

* * * * *